United States Patent [19]

Reinehr et al.

[11] 4,231,962
[45] Nov. 4, 1980

[54] 3-PHENOXYBENZYLIDENEAMINES AND 3-BENZYLBENZYLIDENEAMINES

[75] Inventors: Dieter Reinehr, Kandern, Fed. Rep. of Germany; Laurenz Gsell, Basel, Switzerland

[73] Assignee: Ciba-Geigy Corporation, Ardsley, N.Y.

[21] Appl. No.: 42,756

[22] Filed: May 29, 1979

[30] Foreign Application Priority Data

Jun. 8, 1978 [CH] Switzerland ............................ 6289/78
Apr. 10, 1979 [CH] Switzerland ............................ 3406/79

[51] Int. Cl.³ ............................................. C07C 119/10
[52] U.S. Cl. ........................................ 564/272; 564/274
[58] Field of Search ............... 260/566 R (U.S. only), 260/566 F

[56] References Cited

U.S. PATENT DOCUMENTS

| | | | |
|---|---|---|---|
| 3,468,802 | 9/1969 | Nail | 260/566 F |
| 3,876,701 | 4/1975 | Surrey | 260/566 F |

FOREIGN PATENT DOCUMENTS 46-10165 3/1971 Japan .................................. 260/566 F

OTHER PUBLICATIONS

Patai, Saul, "The Chemistry of the Carbon-Nitrogen Double Bond," p. 476, Interscience Publ. (1979).

*Primary Examiner*—Natalie Trousof
*Assistant Examiner*—L. Hendriksen
*Attorney, Agent, or Firm*—Harry Falber

[57] ABSTRACT

3-Phenoxybenzylideneamines and 3-benzylbenzylideneamines of the formula

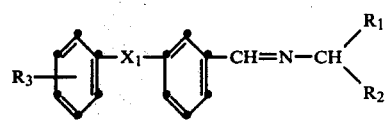

in which $R_1$ is hydrogen or alkyl, $R_2$ is alkyl, with alkyl groups denoted by $R_1$ and $R_2$ together not containing more than 12 C atoms, or $R_1$ and $R_2$ together being alkylene having 4–11 C atoms, $R_3$ is hydrogen, halogen, methyl or methoxy, and $X_1$ is oxygen or —$CH_2$—; a process for obtaining them, and also their use for producing the corresponding aldehydes.

3 Claims, No Drawings

3-PHENOXYBENZYLIDENEAMINES AND 3-BENZYLBENZYLIDENEAMINES

The present invention relates to 3-phenoxybenzylideneamines and 3-benzylbenzylideneamines, to a process for obtaining them, and to their use for producing the corresponding aldehydes.

The compounds according to the invention constitute valuable starting products for producing 3-phenoxybenzaldehydes and 3-benzylbenzaldehydes. These aldehydes for their part are, inter alia, valuable intermediates for producing pyrethroid-like pesticidal compositions, as are described for example in the German Pat. No. 2,231,312. According to this patent specification, 3-phenoxybenzaldehyde can be reacted, in the presence of sodium cyanide or potassium cyanide, directly with cyclopropanecarboxylic acid halides to insecticidal active substances, or 3-phenoxy-α-cyanobenzyl alcohol is reacted with a cyclopropanecarboxylic acid or with a reactive derivative thereof. 3-Phenoxy-α-cyanobenzyl alcohol for its part can be produced by reaction of 3-phenoxybenzaldehyde with sodium cyanide in the presence of acetic acid (see also Swiss Pat. No. 589,051).

By the processes which have become known hitherto, for example by the Sommelet reaction, or by the processes described in 'Monatshefte für Chemie', 67, 24–35 (1936), and in the German 'Offenlegungsschrift' No. 2,624,360, it is not possible to produce straight away for example 3-phenoxybenzaldehyde in the degree of purity required for further application, for example for producing insecticidal active substances of the aforementioned type, so that expensive purifying operations are necessary [see for example the Belgian Pat. No. 857,954]. Furthermore, some of these processes have to be performed under rigorous reaction conditions, or they are unsatisfactory on account of the yield obtained.

There have now been made accessible in a simple manner by the present invention novel intermediates which can be converted under mild, ecologically favourable reaction conditions, and with high yields, into extremely pure 3-phenoxybenzaldehydes and 3-benzylbenzaldehydes, which can be used directly for further reactions.

The compounds according to the invention correspond to the formula

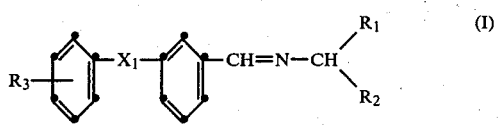

in which
$R_1$ is hydrogen or alkyl,
$R_2$ is alkyl, with alkyl groups denoted by $R_1$ and $R_2$ together not containing more than 12 C atoms, or $R_1$ and $R_2$ together being alkylene having 4–11 C atoms,
$R_3$ is hydrogen, halogen, methyl or methoxy, and
$X_1$ is oxygen or —$CH_2$—.

By halogen in the case of $R_3$ is meant fluorine, chlorine, bromine or iodine, but particularly fluorine or chlorine.

Alkyl groups denoted by $R_1$ and $R_2$ can be straight-chain or branched-chain, and together contain preferably not more than 8, and especially not more than 6, C atoms. The following may be mentioned as examples of alkyl groups $R_1$ and $R_2$ as defined: the methyl, ethyl, n-propyl, isopropyl, n-butyl, sec-butyl, tert-butyl, n-pentyl, 3-pentyl, n-hexyl, 2-heptyl, 3-heptyl, n-octyl, n-decyl and n-dodecyl groups.

If $R_1$ and $R_2$ together form an alkylene chain, this preferably contains 4–7, and particularly 4 or 5, C atoms.

Preferred compounds of the formula I are those wherein $R_1$ is hydrogen or alkyl, $R_2$ is alkyl, with $R_1$ and $R_2$ together not containing more than 6 C atoms, or $R_1$ and $R_2$ together being tetramethylene or pentamethylene, and $R_3$ is hydrogen, fluorine or chlorine. Very particularly preferred compounds of the formula I are those wherein $R_1$ is hydrogen, $R_2$ is α-branched alkyl having up to 6 C atoms, especially isopropyl, and $R_3$ is hydrogen or p-fluorine.

The compounds of the formula I can be produced by the process according to the invention, in a simple and economical manner, by catalytically hydrogenating 3-phenoxybenzonitriles and 3-benzylbenzonitriles to 3-phenoxybenzylamines and 3-benzylbenzylamines, respectively; reacting the 3-phenoxybenzylamines with a compound of the formula II

to a compound of the formula III

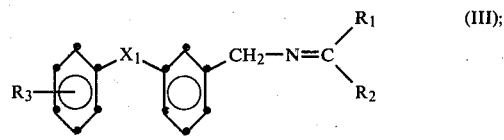

and isomerising the compound of the formula III, in the presence of a catalyst of the formula IV

to a compound of the formula I. In the above formulae II and III, the symbols $R_1$, $R_2$, $R_3$ and $X_1$ have the meanings given under the formula I, X is an alkali metal ion or alkaline-earth metal ion, Y is alkyl having 1–12 C atoms, and n is the charge of the alkali metal ion or alkaline-earth metal ion.

The 3-phenoxybenzonitriles and 3-benzylbenzonitriles as well as the compounds of the formulae II and IV are known, or can be produced by methods known per se.

The catalytic hydrogenation of the nitriles to the amines can be performed in a manner known per se, advantageously in an inert organic solvent, and optionally in the presence of liquid ammonia. Examples of suitable inert organic solvents are: alcohols having up to 6 C atoms, such as methanol, ethanol, propanol, isopropanol, butanols and pentanols; aliphatic and cycloaliphatic hydrocarbons, such as n-pentane, n-hexane and cyclohexane; ethylene glycol- and diethylene glycol- mono- and -dialkyl ethers having 1–4 C atoms in each of the alkyl moieties, such as ethylene glycol- and diethylene glycol-monomethyl ethers and -monoethyl ethers, and ethylene glycol- and diethylene glycol-dimethyl ethers and -diethyl ethers. A preferred solvent is methanol.

The catalysts used can be hydrogenation catalysts which are known per se, such as platinum, rhodium and palladium catalysts. Nickel catalysts, particularly Raney nickel, are preferably used.

Hydrogenation is advantageously performed in a closed system under a pressure of about 10 to 200 bars, and especially under 20 to 130 bars. The hydrogenation temperatures are in general between about 0° and 150° C., and particularly between about 25° and 80° C.

After completion of the reaction and removal of the catalyst and the solvent, the amines can be isolated and purified in the customary manner, for example by means of distillation or extraction with suitable inert organic solvents.

The reaction of the amines with a compound of the formula II, as well as the isomerisation of the compounds of the formula III to compounds of the formula I, are preferably performed in the presence of an inert organic solvent. The inert organic solvents used are especially aprotic organic solvents, above all aliphatic or aromatic hydrocarbons, aliphatic or cyclic ethers, ethylene glycol- and diethylene glycol-di-alkyl ethers having 1–4 C atoms in each of the alkyl moieties, alkyl nitriles or dialkylsulfoxides having up to 4 C atoms in each of the alkyl moieties, N,N-dialkylamides of aliphatic monocarboxylic acids having 1–3 C atoms in the acid moiety, alcohols having at least 4 C atoms, sulfolane, amides of phosphoric acid, and tertiary amines. Examples of solvents of this type are: n-pentane, n-hexane, n-heptane, benzene, toluene, xylenes, diethyl ether, di-n-propyl ether, tetrahydrofuran, tetrahydropyrane, dioxane, ethylene glycol- and diethylene glycol-dimethyl ether and -diethyl ether, dimethylsulfoxide, acetonitrile, propionitrile, butyronitrile, N,N-dimethylformamide, N,N-dimethylacetamide, n-butanol, tert-butanol, n-hexanol, hexamethylphosphoric acid triamide, triethylamine and pyridine. It is also possible to use mixtures of solvents of this kind. Preferred solvents are: dimethylsulfoxide, dioxane, tetrahydrofuran, diethyl ether and, in particular, toluene.

The reaction temperatures for the reaction of the 3-substituted benzylamines with the compound of the formula II are advantageously between about 0° and 80° C., and especially between about 10° and 60° C. Isomerisation of the compounds of the formula III is preferably performed at temperatures between about 20° and 150° C.

The amines and the compound of the formula II are used in at least a stoichiometric amount. It is advantageous to use a slight excess of compound of the formula II, for example an approximately 5–20% excess.

Alkyl groups Y can be straight-chain or branched-chain, and preferably contain 1–6, but particularly 1–4, C atoms. Y is especially preferably tert-butyl. X is for example lithium, potassium, sodium, magnesium, calcium or barium. Preferably, X is an alkali metal, in particular sodium or potassium. Particularly preferred compounds of the formula IV are sodium methylate or potassium methylate, sodium ethylate or potassium ethylate, sodium isopropylate or potassium isopropylate and, in particular, sodium tert-butylate or potassium tert-butylate. The catalysts of the formula IV are advantageously used in an amount of at least 0.1 mol %, relative to the compound of the formula III. Amounts of about 0.5 to 15 mol %, relative to the compound of the formula III, are preferred.

The compounds of the formula I can be converted in a simple manner into highly pure 3-phenoxybenzaldehydes and 3-benzylbenzaldehydes. The invention hence also relates to the use of compounds of the formula I according to the invention for producing 3-phenoxybenzaldehydes and 3-benzylbenzaldehydes by treating the compounds of the formula I with an acid. The conversion of the compounds of the formula I into the aldehydes is performed preferably in an aqueous-organic medium. The acid used is advantageously an inorganic acid, such as hydrochloric acid or sulfuric acid. The acid is in general used in at least a stoichiometric amount, relative to the compound of the formula I, and preferably in excess. As organic solvents, there are preferably used aprotic organic solvents of the aforementioned type, especially toluene. The amines

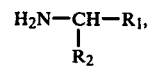

which are formed as by-products during the conversion into the aldehydes, can readily be separated from the reaction medium and further utilised.

The intermediates of the formula III and the compounds of the formula I can be optionally isolated in a manner known per se, for example by means of distillation. An intermediate isolation of this kind is however not essential for producing the aldehydes. A particular advantage of the present invention is that it is possible to produce the aldehydes by way of the novel compounds of the formula I, without noticeable reduction of yield and also without intermediate isolation or purification of the compounds of the formula III and I, in a high degree of purity and with avoidance of complicated oxidation or reduction reactions. The 3-phenoxybenzaldehyde can be converted for example, in the manner initially described, into the 3-phenoxy-α-cyanobenzyl alcohol, or can be used directly for the production of known pyrethroid-like pesticidal compositions.

EXAMPLE 1

(a) Production of 3-phenoxybenzylamine 200 g (1.025 mols) of 3-phenoxybenzonitrile is placed together with 1 liter of methanol, 200 g of liquid ammonia and 50 g of Raney nickel into a steel autoclave. This is then heated to 60° C., and stirring is maintained for one hour with an initial hydrogen pressure of 120 bars. After removal of the mixture from the autoclave, the catalyst is filtered off, the solvent is distilled off at normal pressure, and the residue is distilled in an oil-pump vacuum to obtain 200.3 g (1.01 mols) of 3-phenoxybenzylamine (98.7% strength), corresponding to a yield of 94.7% of theory; b.p. 94° C./3 Pa; $n_D^{20}=1.5946$.

Analysis for $C_{13}H_{13}NO$ (molecular weight 199): calculated: C 78.36%; H 6.58%; N 7.03%; O 8.03%. found: C 78.31%; H 6.61%; N 7.06%; O 8.25%.

MS spectrum: molecular peak 199, masses of the fragments 181, 153, 141, 93, 77, 51.

NMR spectrum $\tau$ [ppm]: 2.6–3.2(m), 6.19(s), 8.58(s) in the ratio of 9:2:2.

(b) Production of N-isobutylidene-(3-phenoxybenzylamine)

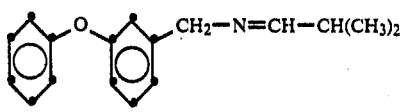

38 g (0.528 mol) of isobutyraldehyde is added dropwise within 30 minutes, with stirring, to a solution of 99.5 g (0.5 mol) of 3-phenoxybenzylamine in 100 ml of toluene. After completion of the dropwise addition, stirring is continued for 20 minutes at room temperature, and the water which has formed (about 8.5 g) is separated in a separating funnel. The toluene with the unreacted isobutyraldehyde and residual water is then removed by rotation in a water-jet vacuum, and the residue is distilled in an oil-pump vacuum to yield 124 g (0.49 mol) of N-isobutylidene-(3-phenoxybenzylamine) as a colourless, mobile liquid, corresponding to a yield of 97.8% of theory; b.p. 85° C./4 Pa; $n_D^{20} = 1.5666$.

Analysis for $C_{17}H_{19}NO$ (molecular weight 253.35): calculated: C 80.60%; H 7.56%; N 5.53%; O 6.31%. found: C 79.91%; H 7.62%; N 5.41%; O 6.52%.

MS spectrum: molecular peak 253, masses of the fragments 184, 183, 168, 153, 77.

NMR spectrum $\tau$ [ppm]: 2.47(d), 2.6–3.2(m), 5.50(s), 7.51(m), 8.97(d) in the ratio of 1:9:2:1:6.

(c) Production of 3-phenoxybenzylidene-isobutylamine

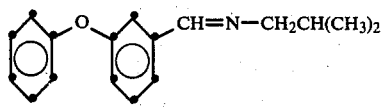

51 g (0.202 mol) of N-isobutylidene-(3-phenoxybenzylamine) is dissolved in 45 ml of dimethyl sulfoxide, and at room temperature (20°–25° C.) is added all at once, with stirring, 2 g (0.0179 mol) of potassium-tert-butylate. The temperature of the reaction solution rises during this addition to 25°–30° C. The solution is stirred for a further hour at room temperature, and is then extracted three times with 50 ml of water each time. The residue is taken up in 30 ml of diethyl ether, dried with magnesium sulfate, and distilled to obtain 48.5 g (0.192 mol) of 3-phenoxybenzylidene-isobutylamine, corresponding to a yield of 95% of theory; b.p. 83° C./4 Pa; $n_D^{20} = 1.5677$.

Analysis for $C_{17}H_{19}NO$ (molecular weight 253.35): calculated: C 80.60%; H 7.56%; N 5.53%; O 6.31%. found: C 80.65%; H 7.73%; N 5.50%; O 6.33%.

MS spectrum: molecular peak 253, masses of the fragments 238, 210, 183, 117, 77.

NMR spectrum $\tau$ [ppm]: 1.83(s), 2.5–3.1(m), 6.59(dd), 8.00(sept), 9.02(d) in the ratio of 1:9:2:1:6.

(d) Conversion into 3-phenoxybenzaldehyde 20 g of 37% hydrochloric acid (about 0.2 mol) and 20 ml of water are added, with stirring, to a solution of 40 g (0.158 mol) of 3-phenoxybenzylidene-isobutylamine in 40 ml of toluene, and the whole is refluxed for 15 minutes. The organic phase is separated; it is then washed neutral with 10% sodium hydrogen carbonate solution, and the toluene is removed by rotation in a slight water-jet vacuum. Distillation of the residue yields 29.7 g (0.15 mol) of 3-phenoxybenzaldehyde, corresponding to a yield of 94.9% of theory; b.p. 94° C./6 Pa; $n_D^{20} = 1.5976$.

The 3-phenoxybenzaldehyde obtained can be used directly, that is to say, without additional purification operations, for the production of pyrethroid-like pesticidal compositions or 3-phenoxy-α-cyanobenzyl alcohols, for example by the process described in the German Pat. No. 2,231,312. Also properties and application of the insecticidal active substances obtainable by this process are described in the patent specification mentioned.

There are produced in an analogous manner from

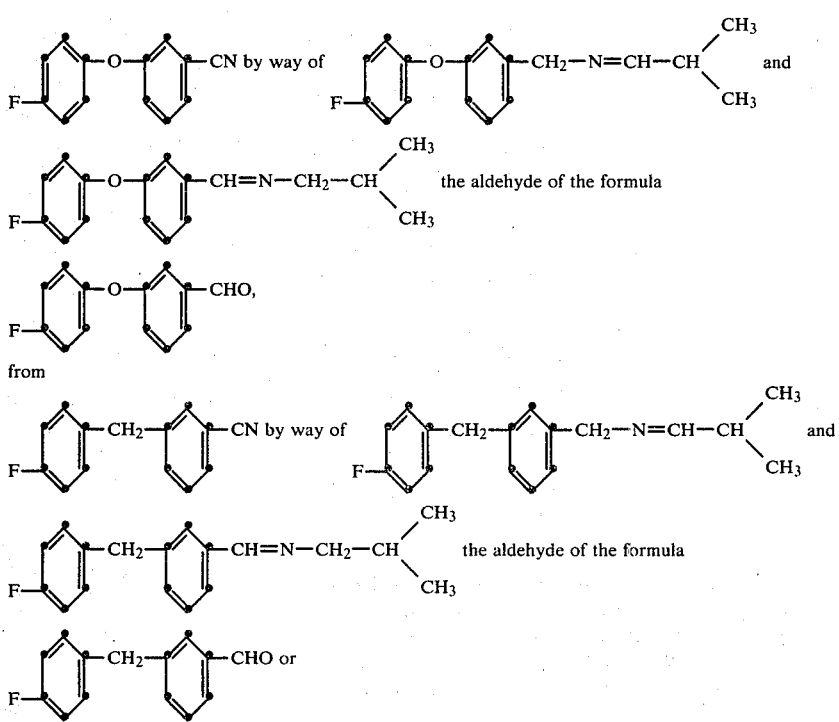

from

PhCH2-C6H4-CN by way of PhCH2-C6H4-CH2-N=CH-CH(CH3)2 and

PhCH2-C6H4-CH-N-CH2-CH(CH3)2 the aldehyde of the formula

PhCH2-C6H4-CHO

EXAMPLE 2

80 g (0.316 mol) of N-isobutylidene-3-phenoxybenzylamine is dissolved in 80 ml of toluene; to the solution is then added 4 g (0.036 mol) of potassium-tert-butylate, and the mixture is refluxed for 4 hours. After cooling of the reaction mixture, 35 g of 37% hydrochloric acid (about 0.35 mol) and 50 ml of water are added, and the toluene phase is separated. The toluene is distilled off to leave 57 g (0.288 mol) of 3-phenoxybenzaldehyde, corresponding to a yield of 91% of theory.

EXAMPLE 3

The procedure is carried out as described in Example 1(b) except that 50 g (0.25 mol) of 3-phenoxybenzylamine and 30 g (0.348 mol) of diethyl ketone are used. There is obtained after distillation 62.5 g (0.234 mol) of N-3-pentylidene-(3-phenoxybenzylamine), corresponding to a yield of 93.6% of theory; b.p. 128° C./5 Pa.

Analysis for $C_{18}H_{21}NO$ (molecular weight 267.37): calculated: C 80.86%; H 7.92%; N 5.24%; O 5.98%. found: C 80.97%; H 7.88%; N 5.36%; O 5.92%.

MS spectrum: molecular peak 267, masses of the fragments 238, 183, 85, 83.

NMR spectrum $\tau$ [ppm]: 2.6–3.3(m), 5.51(s), 7.70(m), 8.90(m) in the ratio of 9:2:4:6.

60.5 g (0.226 mol) of N-3-pentylidene-(3-phenoxybenzylamine) is dissolved in 50 ml of toluene; to the solution is then added 2 g (0.0179 mol) of potassium tert-butylate, and the mixture is refluxed for 4 hours. After cooling of the reaction mixture, extraction is effected by shaking with 50 ml of water, and the organic phase is separated in a separating funnel. The toluene is distilled off in a slight water-jet vacuum to leave 56 g (0.21 mol) of 3-phenoxybenzylidene-3-pentylamine, corresponding to a yield of 92.5% of theory; b.p. 125° C./Pa.

Analysis for $C_{18}H_{21}NO$ (molecular weight 267.37): calculated: C 80.86%; H 7.92%; N 5.24%; O 5.98%. found: C 81.19%; H 8.08%; N 5.43%; O 6.27%.

NMR spectrum $\tau$ [ppm]: 1.86(s), 2.4–3.1(m), 7.13(quin), 8.38(quin), 9.13(t) in the ratio of 1:9:1:4:6.

EXAMPLE 4

The procedure is carried out as described in Example 1(b) but with the use of 38 g (0.528 mol) of n-butyraldehyde instead of isobutyraldehyde. Distillation leaves 65 g (0.257 mol) of N-butylidene-(3-phenoxybenzylamine), corresponding to a yield of 51.4% of theory; b.p. 90°–92° C./5 Pa.

Analysis for $C_{17}H_{19}NO$ (molecular weight 253.35): calculated: C 80.60%; H 7.56%; N 5.53%; O 6.31%. found: C 80.75%; H 7.68%; N 5.28%; O 6.53%.

NMR spectrum $\tau$ [ppm]: 2.3(t), 2.6–3.2(m), 5.5(s), 7.7(m), 8.5(m), 9.05(t) in the ratio of 1:9:2:2:2:3.

The isomerisation of N-butylidene-(3-phenoxybenzylamine) [60 g, 0.237 mol] is performed in a manner analogous to that described in Example 3. Distillation leaves 56.5 g (0.223 mol) of 3-phenoxybenzylidene-n-butylamine, corresponding to a yield of 94.1% of theory; b.p. 134°–135° C./13 Pa.

Analysis for $C_{17}H_{19}NO$ (molecular weight 253.35): calculated: C 80.60%; H 7.56%; N 5.53%; O 6.31%. found: C 80.67%; H 7.72%; N 5.80%; O 6.42%.

NMR spectrum $\tau$ [ppm]: 1.81(s), 2.4–3.1(m), 6.42(t), 8.1–8.8(m), 9.03(t) in the ratio of 1:9:2:4:3.

EXAMPLE 5

The procedure is carried out as described in Example 1(b) but with the use of 50 g (0.25 mol) of 3-phenoxybenzylamine and 25 g (0.255 mol) of cyclohexanone. Distillation leaves 41 g (0.147 mol) of N-cyclohexylidene(3-phenoxybenzylamine), corresponding to a yield of 58.7% of theory; b.p. 135°–136° C./4 Pa.

Analysis for $C_{19}H_{21}NO$ (molecular weight 279.38): calculated: C 81.69% H 7.58% N 5.01% O 5.73% found: C 80.81% H 7.56% N 5.02% O 6.12%.

NMR spectrum $\tau$ [ppm]: 2.6–3.2(m), 5.51(s), 7.65(m), 8.33(m) in the ratio of 9:2:4:6.

50 g (0.179 mol) of N-cyclohexylidene-(3-phenoxybenzylamine) is isomerised in the manner described in the preceding Examples. Distillation yields 46 g (0.165 mol) of 3-phenoxybenzylidene-cyclohexylamine, corresponding to a yield of 92% of theory; b.p. 150° C./10 Pa; m.p. 72°–74° C.

Analysis for $C_{19}H_{21}NO$ (molecular weight 279.38): calculated: $C_{81.69}$%; H 7.58%; N 5.01%; O 5.73%. found: C 81.96%; H 7.78%; N 5.13%; O 5.83%.

NMR spectrum $\tau$ [ppm]: 1.78(s), 2.5–3.1(m), 6.84(m), 8.1–8.8(m) in the ratio of 1:9:1:10.

What is claimed is:

1. A compound of the formula $R_3$-C6H3-$X_1$-C6H4-CH=N-CH($R_1$)($R_2$)  (I)

in which $R_1$ is hydrogen or alkyl, $R_2$ is alkyl, with alkyl groups denoted by $R_1$ and $R_2$ together not containing more than 12 C atoms, or $R_1$ and $R_2$ together being alkylene having 4–11 C atoms, $R_3$ is hydrogen, halogen, methyl or methoxy, and $X_1$ is oxygen or $-CH_2-$.

2. A compound according to claim 1, wherein $R_1$ is hydrogen or alkyl, and $R_2$ is alkyl, with $R_1$ and $R_2$ together not containing more than 6 C atoms, or $R_1$ and $R_2$ together being tetramethylene or pentamethylene, $R_3$ is hydrogen, fluorine or chlorine, and $X_1$ is oxygen or $-CH_2-$.

3. A compound according to claim 1, wherein $R_1$ is hydrogen, and $R_2$ is α-branched alkyl having up to 6 C atoms, particularly isopropyl, $R_3$ is hydrogen or p-fluorine, and $X_1$ is oxygen or $-CH_2-$.

* * * * *